United States Patent [19]
Bonfils et al.

[11] Patent Number: 5,679,668
[45] Date of Patent: Oct. 21, 1997

[54] METHOD OF CONTROLLING FERTILITY IN MALES WITH 20-SUBSTITUTE OF STEROIDS

[75] Inventors: Armelle Bonfils, Paris; Daniel Philibert, La Varenne Saint Hilaire, both of France

[73] Assignee: Roussel Uclaf, France

[21] Appl. No.: 691,667

[22] Filed: Aug. 2, 1996

Related U.S. Application Data

[62] Division of Ser. No. 403,276, Mar. 13, 1995.

[30] Foreign Application Priority Data

Apr. 1, 1994 [FR] France ................... 94 03872

[51] Int. Cl.$^6$ .................. A61K 31/575; A61K 31/58; A61K 31/585
[52] U.S. Cl. .................. 514/182; 514/174; 514/175; 514/176; 514/172
[58] Field of Search .................. 514/172, 174, 514/175, 176, 182

[56] References Cited

FOREIGN PATENT DOCUMENTS 1380424 10/1964 France.
  90805  1/1968 France.

Primary Examiner—Kimberly J. Prior
Attorney, Agent, or Firm—Bierman, Muserlian and Lucas LLP

[57] ABSTRACT

The invention is a method of controlling fertility in male warm-blooded animals by administering a compound of the formula

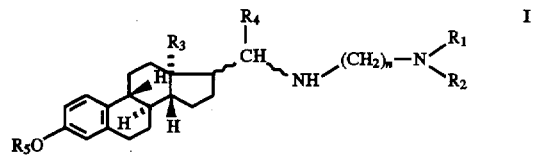

wherein $R_1$ and $R_2$ are individually selected from the group consisting of alkyl of 1 to 12 carbon atoms and aralkyl of 7 to 15 carbon atoms or taken together form a saturated heterocycle of 5 to 6 ring members optionally having a second ring heteroatom selected from the group consisting of sulfur, oxygen and nitrogen, $R_3$ is an α-alkyl of 1 to 8 carbon atoms, n is an integer from 2 to 15, $R_4$ is alkyl of 1 to 12 carbon atoms, $R_5$ is selected from the group consisting of hydrogen, alkyl of 1 to 12 carbon atoms and acyl of an organic carboxylic acid of up to 12 carbon atoms and the wavy lines indicate that the 17- and 20- asymmetrical centers are independent of the absolute R and S configurations and their non-toxic, pharmaceutically acceptable acid addition salts.

5 Claims, No Drawings

METHOD OF CONTROLLING FERTILITY IN MALES WITH 20-SUBSTITUTE OF STEROIDS

PRIOR APPLICATION

This application if a division of U.S. patent application Ser. No. 403,276 filed Mar. 3, 1995.

OBJECTS OF THE INVENTION

It is an object of the invention to provide the novel steroids of formula I and their non-toxic, pharmaceutically acceptable acid addition salts and a novel process and novel intermediates for their preparation.

It is another object of the invention to provide novel compositions and a method for controlling fertility in male warm-blooded animals.

These and other objects and advantages of the invention will become obvious from the following detailed description.

THE INVENTION

The novel 20-substituted steroids of the invention are selected from the group consisting of a compound of the formula

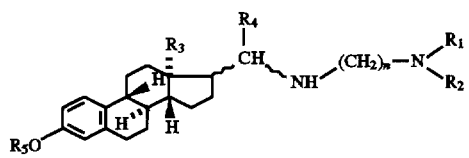

wherein $R_1$ and $R_2$ are individually selected from the group consisting of alkyl of 1 to 12 carbon atoms and aralkyl of 7 to 15 carbon atoms or taken together form a saturated heterocycle of 5 to 6 ring members optionally having a second ring heteroatom selected from the group consisting of sulfur, oxygen and nitrogen. $R_3$ is an α-alkyl of 1 to 8 carbon atoms, n is an integer from 2 to 15, $R_4$ is alkyl of 1 to 12 carbon atoms, $R_5$ is selected from the group consisting of hydrogen, alkyl of 1 to 12 carbon atoms and acyl of an organic carboxylic acid of up to 12 carbon atoms and the wavy lines indicate that the 17- and 20- asymmetrical centers are independent of the absolute R and S configurations and their non-toxic, pharmaceutically acceptable acid addition salts.

Examples of $R_1$, $R_2$, $R_4$ and $R_5$ as alkyl of 1 to 12 carbon atoms are methyl, ethyl, propyl, isopropyl, butyl, isobutyl, tert-butyl, n-pentyl, n-hexyl, 2-methyl pentyl, 2,3-dimethylbutyl, n-heptyl, 2-methylhexyl, 2,2-dimethylpentyl, 3,3-dimethyl-pentyl, 3-ethyl-pentyl, n-octyl, 2,2-dimethylhexyl, 3,3-dimethylhexyl, 3-methyl-3-ethylpentyl, nonyl, 2,4-dimethylheptyl and n-decyl, preferably methyl, ethyl or isopropyl. When $R_1$ and $R_2$ is aralkyl of 7 to 15 carbon atoms, it is preferably benzyl or phenethyl.

Examples of $R_1$ and $R_2$ forming with the nitrogen to which they are linked a saturated heterocycle with 5 or 6 ring members optionally containing another hetero ring atom chosen from oxygen, nitrogen and sulfur are piperidino, morpholino, thiomorpholino, piperazino and pyrrolidino.

Examples of $R_3$ as alkyl of 1 to 8 carbon atoms are methyl, ethyl, propyl, isopropyl, butyl, isobutyl, tert-butyl, n-pentyl, n-hexyl, 2-methyl-phenyl, 2,3-dimethyl-butyl, n-heptyl, 2-methylhexyl, 2,2-dimethylpentyl, 3,3-dimethylpentyl and 3-ethylpentyl, preferably methyl.

Examples of acyl of an organic carboxylic acid of up to 12 carbon atoms are acetyl, propionyl, butyryl, benzoyl, valeryl, hexanoyl, acryloyl and crotonoyl as well as formyl.

Examples of acids for the formation of non-toxic, pharmaceutically acid addition salts are hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane or ethane sulfonic acid, arylsulfonic acids such as benzene or p-toluene sulfonic acid and arylcarboxylic acids. The addition salts of hydrochloric acid are preferred.

Among the preferred compounds are those of formula I wherein n is 2 and those of the formula

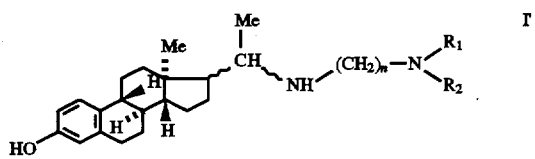

wherein $R_1$ and $R_2$ are defined above and their non-toxic, pharmaceutically acceptable acid addition salts.

Specific preferred compounds of formula I are (20R) (8α,9β,13α,14β,17α) 20-[((dimethylamino)-ethyl)-amino]-19-nor-$\Delta^{1,3,5,(10)}$-pregnatrien-3-ol, (20S) (8α,9β,13α,14β,17α) 20-[((dimethylamino)-ethyl)-amino]-19-nor-$\Delta^{1,3,5,(10)}$-pregnatrien-3-ol, (20R) (8α,9β,13α,14β,17α) 20-[((dimethylamino)-ethyl)-amino]-19-nor-$\Delta^{1,3,5,(10)}$-pregnatrien-3-ol, (20S) (8α,9β,13α,14β,17α) 20-[((dimethylamino)-ethyl)-amino]-19-nor-$\Delta^{1,3,5,(10)}$-pregnatrien-3-ol, as well as their acid addition salts. Most preferred is (20S) (8α,9β,13α,14β,17α) 20-[((dimethylamino)-ethyl)-amino]-19-nor- $\Delta^{1,3,5,(10)}$-pregnatrien-3-ol and its acid addition salts.

The novel process of the invention for the preparation of the compounds of formula I comprises subjecting a compound of the formula

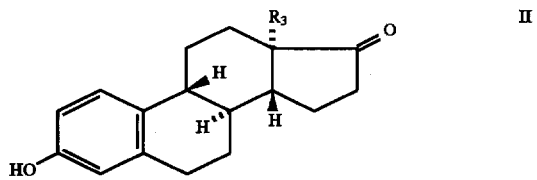

wherein $R_3$ is defined as above to an acylation agent or alkylation agent to obtain a compound of the formula

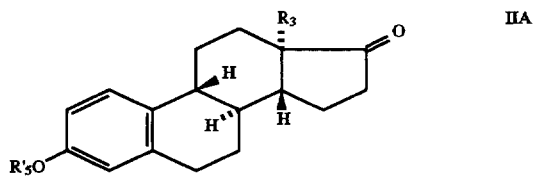

wherein $R_3$ is defined as above and $R'_5$ is alkyl of 1 to 12 carbon atoms or acyl of an organic carboxylic acid of up to 12 carbon atoms, reacting a compound of formula II or IIA with a cyanidation agent to form a compound of the formula

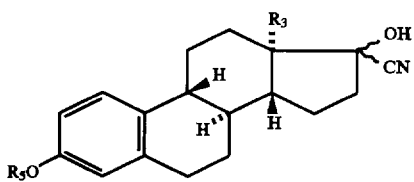

in which $R_3$ and $R_5$ have the same meanings as above and in which the wavy line indicates that the product is presented in the form of pure stereoisomers (17α-OH, 17β-CN) or (17α-CN, 17β-OH) or in the form of a mixture thereof, subjecting the latter to a dehydration reaction to obtain a compound of the formula

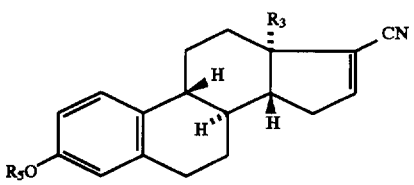

in which $R_3$ and $R_5$ have the above meanings, reducing the 16–17 double bond to obtain a compound of the formula

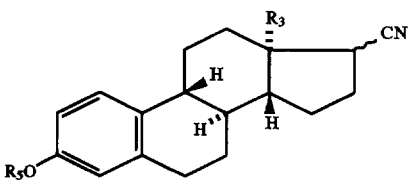

wherein the wavy line indicates that the —CN is in position 17α or 17β, or in the form of a 17α and 17β mixture, and $R_3$ and $R_5$ have the above meanings, reacting the latter with an organometal reagent of $R_4$ as defined above, then to the action of an acid hydrolysis agent to obtain a compound of the formula

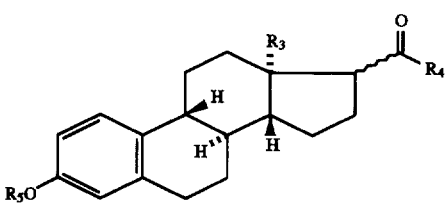

wherein $R_3$, $R_4$ and $R_5$ have the above meanings and in which the wavy line indicates that the —COR$_4$ is in position 17α or 17β, or in the form of a 17α and 17β mixture, reacting the latter with a hydroxyl-amine salt to obtain a compound of the formula

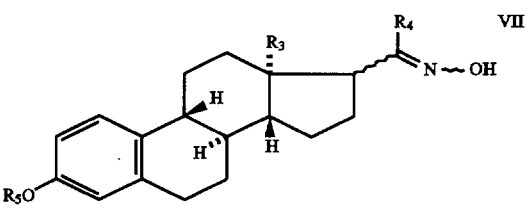

wherein, $R_3$, $R_4$ and $R_5$ have the above meanings and in which the wavy line indicates that —C(R$_4$)=N—OH is in 17α or 17β position or in the form of a 17α and 17β mixture, and the oxime is in the syn or anti position, or in the form of a syn and anti mixture, reducing the oxime to obtain a compound of the formula

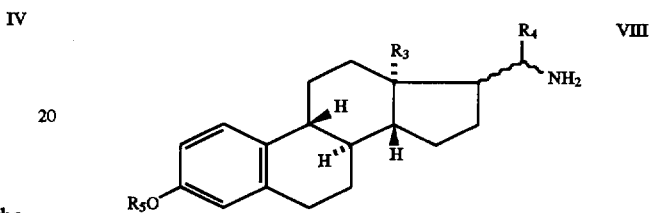

wherein the wavy line indicates that —NH$_2$ is in 20R or 20S position or in the form of a 20R and 20S mixture, and $R_3$, $R_4$ and $R_5$ have the above meanings, reacting the latter with an acyl halide of the formula $$X—CO—(CH_2)_{n'}—NR_1R_2$$

wherein X is halogen, $R_1$ and $R_2$ are as defined above, n' is equal to n-1, n being defined as above, then, optionally to a selective hydrolysis in the 3-position of the diacylated compound formed to obtain a compound of the formula

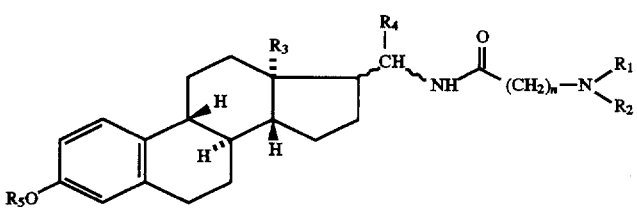

wherein the wavy lines, $R_1$, $R_2$, $R_3$, $R_4$, $R_5$ and n' have the above meanings, reducing the keto group of the said amide, and optionally to one or more of the following reactions in any order:

acylation in position 3,
alkylation in position 3,
saponification of acyloxy in position 3,
separation of the different stereoisomers,
salification with an organic or mineral acid to obtain the compound of formula I.

The acylation agent is preferably a carboxylic acid derivative, for example acid chloride or an anhydride in the presence of a base such as pyridine. The optional alkylation is carried out by the usual methods with an alkylation agent such as preferably an alkyl halide like alkyl iodide or alkyl sulfate.

The cyanidation agent is preferably sodium or potassium cyanide and the cyanidation reaction is preferably carried out in a lower alcohol such as methanol in the presence of acetic acid. The dehydration reaction can be carried out using a dehydration agent such as phosphorus oxychloride in pyridine.

The reduction of the 16–17 double bond can be carried out either by catalytic hydrogenation with the hydrogenation agent being hydrogen in the presence of catalysts such as palladium on charcoal, or a rhodium reagent such as Wilkinson reagent, or by the action of sodium borohydride in ethanol, or by the action of magnesium in methanol. This reduction is either stereospecific and allows the >CH- substituent to be obtained in position 17α or in position 17β, or it is non-stereospecific in which a mixture of stereoisomers (17α+17β) is obtained which is optionally separated by standard methods such as crystallization or chromatography.

The organometal reagents which are derivatives of $R_4$ are standard reagents such as an organolithium compound ($R_4$—Li), an organomagnesium compound ($R_4$—Mg—X) with X being halogen chosen from Cl, Br and I, preferably Br.

The acid hydrolysis reaction which follows the reaction with the organometal allows the intermediate imine formed to be hydrolyzed which hydrolysis is carried out under standard conditions for imine hydrolysis in an acid medium such as hydrochloric acid, oxalic acid or acetic acid.

Formation of the oxime of formula VII is preferably carried out by the action of hydroxylamine hydrochloride in the presence of a base such as pyridine, sodium hydroxide or sodium carbonate.

The reduction of the product of formula VII can be carried out by different methods such as catalytic hydrogenation with, as hydrogenation reagent, hydrogen in the presence of catalysts such as palladium on charcoal or platinum dioxide, by the action of zinc in an acetic medium, by sodium in an alcohol such as ethanol or n-propanol, or also by the addition of diborane in diglyme. This reduction is either stereospecific and allows the product in position 20R or in position 20S to be obtained, or it is non-stereospecific wherein a mixture of 20R+20S stereoisomers is obtained which is optionally separated by standard methods such as crystallization or chromatography.

The condensation of the compound of formula X—CO—$(CH_2)_n{'}$—$NR_1R_2$ in which X is halogen chosen from Cl, Br and I and n', $R_1$ and $R_2$ are as described previously with the compound of formula VIII is carried out in a basic medium, preferably in an aprotic dipolar solvent such as dimethylformamide (DMF). The reaction is preferably carried out in a triethylamine/dimethylformamide (TEA/DMF) medium.

The selective hydrolysis of the 0-acyl compound which is optionally formed intermediately is carried out under the usual conditions using an agent which can be an alkaline base such as sodium hydroxide or potassium hydroxide in a lower alcohol such as methanol or ethanol.

The reduction of the keto group of the amide of formula IX is carried out for example by means of a metal hydride such as lithium aluminum hydride ($AlLiH_4$) in an aprotic polar solvent such as tetrahydrofuran (THF) or ether or by means of alkali metal borohydrides such as sodium borohydride ($NaBH_4$) in the presence of acids such as acetic acid.

If desired and if necessary, the acylation or alkylation reactions of the 3 —OH group are carried out by the methods as described previously. The optional saponification reaction is preferably carried out in the presence of an alkali metal base such as sodium hydroxide or potassium hydroxide, potassium terbutylate or lithium acetylide in ethylene amine. The saponification reaction takes place preferably in a lower alcohol such as methanol or ethanol.

The optional separation of the different stereoisomers is carried out by standard methods of crystallization or chromatography. The salification with an acid is carried out under the usual conditions preferably with hydrochloric acid for example in an ethereal solution.

During the action of a cyanidation agent leading to the product of formula III, with an organometal reagent leading to the product of formula VI or of the hydroxylamine salt leading to the product of formula VII, a product of formulae III, VI or VII can be obtained in which the acyloxy group is hydrolyzed.

The invention extends to a process as defined previously in which the product of formulae III, VI or VII in which the acyloxy group has been hydrolyzed, is optionally reacylated.

The products of formulae V, VI, VII, VIII and IX are optionally obtained in the form of a mixture of stereoisomers which can optionally be subjected to operations which separate these stereoisomers. The invention extends to a process as defined previously in which the different stereoisomers obtained during preparation processes of the products of formulae V, VI, VII, VIII and IX are optionally separated.

The compositions of the invention for controlling fertility in male warm-blooded animals are comprised of an amount of a compound of formula and its non-toxic, pharmaceutically acceptable acid addition salts sufficient to control fertility and an inert pharmaceutical carrier. The compositions may be in the form of tablets, dragees, capsules, granules, suppositories, gels, creams, implants, microspheres, patches and injectable solutions or suspensions.

Examples of suitable inert pharmaceutical carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions of the invention have 1) a strong affinity for the Sigma receptors (see the pharmacological tests) or 2) an activity vis-a-vis the influx of the calcium into the spermatozoid. The results of tests show that among the products which fix to the Sigma receptors, certain act by stimulating the influx of calcium into the spermatozoid and others by inhibiting the influx of calcium stimulated or not by progesterone, a molecule described as binding to the Sigma receptor.

The products of formula I having an agonist activity stimulate the influx of calcium into the spermatozoid. The corresponding compositions of the invention can be used in the treatment of certain forms of sterility characterized by an insufficient fertilizing power of the spermatozoids.

The products of formula I having an antagonist activity inhibit the influx of calcium into the spermatozoid. The corresponding compositions of the invention are therefore of use in controlling the acrosomial reaction and consequently affect the fertilizing power of the spermatozoid. They can therefore be used as a contraceptive and in particular as a male contraceptive.

They can also be used in the veterinary domain as a male contraceptive in domestic animals (dogs, cats ...) or to limit the proliferation of any pests, in particular rodents or pigeons.

The method of the invention for controlling fertility in male warm-blooded animals comprises administering to male warm-blooded animals an amount of a compound of formula I or its acid addition salts in an amount sufficient to control fertility. The compounds may be administered orally, rectally or parenterally and the usual daily dose is 0.10 to 13.5 mg/kg depending on the specific compound, method of administration and the condition treated.

The compound of formula II is available by the processes described by Hutchinson et al., Tetrahedron Letters, 1985, Vol. 26(15), pp. 1819–1822 and Smith et al, J. Am. Chem. Soc., 1966, pp. 3120–3128.

The intermediates of formulae $II_A$, III, IV, V, VI, VII, VIII and IX are novel and a part of the invention with the exception of compounds of formula $II_A$ in which $R'_5$ is an alkyl group containing at most 12 carbon atoms.

In the following examples, there are described several preferred embodiments to illustrate the invention. However, it should be understood that the invention is not intended to be limited to the specific embodiments.

EXAMPLE 1

(20S) (8α,9β,13α,14β,17 α) 20-((dimethylamino)-ethyl)-amino-19-nor-$\Delta^{1,3,5(10)}$-pregnatrien-3-ol Stage A: 8α,9β,13α,14β 3-acetyloxy-$\Delta^{1,3,5(10)}$-estratrien 17-one 33.5 ml of acetic anhydride were added to a suspension of 33.3 g of antipodal estrone (preparation as described in Hutchinson et al., Tetrahedron Letters, 1985, Vol. 26(15), pp. 1819–1822) in 67 ml of pyridine. A slightly exothermic dissolution was observed with the temperature rising from 18° C. to 32° C. The mixture was stirred for 18 hours at 18±2° C. and then was poured into a mixture of ice-cooled water (660 ml)/22° Be hydrochloric acid (76 ml). After crystallization, the suspension stood for 1 hour, was filtered, washed with water and dried to obtain 38.7 g of the expected crude product which was purified by hot and cold crystallization from 83 ml of absolute alcohol, followed by treatment with L2S activated charcoal. After filtration and drying, 32.7 g of the desired product were obtained with a melting point of 128° C.

Stage B: (8α,9β,13α,14β,17α) 3-(acetyloxy)-17-hydroxy-$\Delta^{1,3,5(10)}$-estratrien-17-carbonitrile 91.6 g of potassium cyanide were introduced under an inert gas into a solution of 32.7 g of estrone acetate of Stage A in 654 ml of methanol and 167 ml of acetic acid, and the mixture was stirred for 16 hours at ambient temperature. Then, 330 ml of an ice-water mixture were added to the suspension and after significant crystallization had been observed, the reaction medium was poured into 3 liters of ice-cooled water, followed by filtering and washing with water. The undried crude product was dissolved in 1.2 liters of ethyl acetate and the organic phase was washed, dried, filtered and concentrated until crystallization. After cooling down to −10° C. for 1 hour, filtering was carried out followed by washing and drying to obtain 27.2 g of the expected product melting at 198–200° C.

Stage C: (8α,9β,13α,14β,17α)$\Delta^{1,3,5(10)}$16 -estra-tetraene-3-ol-17-carbonitrile 27.2 g of the product of Stage B in 82 ml of pyridine and 25 ml of phosphorus oxychloride were refluxed for 4 hours and then, the reaction medium was cooled to 20° C. and poured over 450 ml of crushed ice. After an exothermic precipitation had been observed, sulfuric acid diluted to ⅕ was added to obtain a pH close to 1. Extraction was carried out with ethyl acetate, followed by washing with water, then with a solution of sodium bicarbonate, drying, filtering and evaporating to dryness under reduced pressure. The residue was dissolved in 60 ml of ethanol and then the solution was stirred for 1 hour at 0° C., followed by filtering and drying to obtain 17.7 g of the expected product melting at 120° C.

Stage D: (8α,9β,13α,14β,17α)-$\Delta^{1,3,5(10)}$-estratriene-3-ol-17-carbonitrile 1.425 liters of hydrogen were introduced over 14 minutes under nitrogen into a suspension of 17.7 g of the product of Stage C in 354 ml of ethyl acetate and 8.85 g of 10% palladium hydroxide on charcoal and the mixture was stirred for 30 minutes. After filtering and evaporating to dryness under reduced pressure, the dry extract was dissolved in 90 ml of ethanol, stirred for one hour at a temperature of −10° C., followed by separation and drying to obtain 15.35 g of the expected product melting at 144.5° C. and having a specific rotation of $[\alpha]_D$=−100° (c=1% in $CHCl_3$).

Stage E: (8α,9β,13α,14β,17 α)-19-nor-$\Delta^{1,3,5(10)}$-pregnatrien-3-ol-20-one 121 ml of methyl iodide were added at reflux over one hour to a mixture of 46 g of magnesium turnings in 307 ml of benzene and 307 ml of ether under inert gas. The reaction medium was refluxed for 30 minutes and a solution, prepared extemporaneously, of 15.35 g of the product of Stage D in 154 ml of benzene and 154 ml of ether, was introduced. The mixture was stirred at reflux for 93 hours and after reflux was stopped, the suspension was slowly poured into a water/ice mixture, and 340 ml of acetic acid (pH=4) were added. After concentration, separation was carried out followed by washing and drying to obtain 13.7 g of crude product which was purified in 840 ml of acetone and 0.6 g of 3SA activated charcoal, filtered, concentrated to 5 vol., stirred for one hour at a temperature of −10° C., separated and dried to obtain 12.2 g of the expected product melting at 248° C. and having a specific rotation of $[\alpha]_D$=−156.6° (c=0.5% in $CHCl_3$).

Stage F: (8α,9β,13α,14β,17α) 20-hydroxyimino-19-nor-$\Delta^{1,3,5(10)}$-pregnatrien-3-ol 4.5 g of hydroxylamine hydrochloride were added to a solution, under nitrogen, of 10 g of the product of Stage E in 100 ml of pyridine and the mixture was heated to 80–85° C. for 90 minutes. Then, 310 ml of demineralized water were added and crystallization of the product was observed. The crystals were separated and crystallized from 120 ml of ethanol at reflux. Another 75 ml of demineralized water were added and significant crystallization of the product was observed. The mixture was stirred for 30 minutes at 0° C., followed by separation and drying to obtain 9.45 g of the expected product melting at 234° C. Stage G: (20S)(8α,9β, 13α,14β,17α) 20-amino-19-nor-$\Delta^{1,3,5(10)}$-pregnatrien-3-ol 7.35 g of the product of Stage F in 550 ml (+368 ml for rinsing) of acetic acid were added to a suspension of 2.94 g of platinum dioxide in 304 ml of acetic acid and hydrogenation was carried out with a total absorbed volume of 1075 ml of hydrogen over 6 hours and 30 minutes.

Obtaining the hydrochloride

After filtration, concentration under reduced pressure was carried out until a dry extract was obtained which was taken up in an acid medium of a mixture of 4.15 ml of hydrochloric acid in 53.5 ml of ethanol and 1.2 ml of water. 92 ml of ether were added to the solution which was stirred at 0° C. for 1 hour, followed by separation and drying. The crude hydrochloride was crystallized by dissolution at reflux in 50 ml of ethanol with 0.5% hydrochloric acid and stirring for 1 hour at 0+5° C. followed by separation.

Obtaining the base 140 ml of demineralized water were slowly added hot to a solution of the said hydrochloride purified in a basic mixture of 11 ml of triethylamine, 64 ml of ethanol and 27 ml of water at reflux. Crystallization was observed and the mixture was stirred for 1 hour at 0+5° C., followed by separation and drying to obtain 3.77 g of the crude base which was purified by dissolution at reflux in 120 ml of ethanol, concentration at normal pressure and under nitrogen to a volume of 40 ml, stirring for 1 hour at 0+5° C., separation and drying to obtain 3.285 g of the expected product melting at 235° C.

Stage H: (20S) (8α,9β,13α,14β,17α) 2-dimethylamino-N-(19-nor-$\Delta^{1,3,5(10)}$-pregnatrien-3-ol-20-yl)-acetamide 12 g of the hydrochloride of N,N dimethyl-glycine chloride were added rapidly under inert gas to a solution of the product of Stage G in 91.5 ml of dimethylformamide and 28.4 ml of triethylamine, obtained at 80° C., then cooled to +5° C., followed by stirring for 3 hours. The mixture was poured into a saturated solution of 370 ml of sodium bicarbonate in 550 ml of ice+water. The mixture was stirred for 1 hour followed by extraction 3 times with 100 ml of dichloromethane and washing with water, then with a solution of sodium bicarbonate, then with a solution of salt water. The combined organic solutions were concentrated under reduced pressure until a dry extract of 6 g was obtained.

The residue was taken up under inert gas in 37 ml of methanol and 11 ml of 5N sodium hydroxide, followed by stirring for 1 hour until total dissolution. 220 ml of demineralized water were added slowly and carbon dioxide (pH 8) was bubbled through. 14.7 ml of triethylamine were added and the mixture was stirred for 15 minutes, followed by extraction with 250 ml, then 100 ml of dichloromethane, washing 5 times with 100 ml of water. The organic solution was dried, treated on 3SA activated charcoal, filtered, concentrated under reduced pressure until a dry extract (oil) was obtained which was crystallized by two entrainments with ethanol to obtain 6.15 g of the expected crude product which was dissolved at reflux in 80 ml of ethanol, treated with L2S activated charcoal, filtered and concentrated at normal pressure to a volume of 40 ml. Crystallization was observed and 10 ml of water were added. The mixture was stirred for 1 hour at 0°+5° C., followed by separation and drying to obtain 3.03 g of the expected product melting at 226° C.

Stage I: (20S) (8α,9β,13α,14β,17α) 20-(((dimethylamino)-ethyl)-amino-19-nor-$\Delta^{1,3,5(10)}$-pregnatrien-3-ol 3.03 g of the product of Stage H were added at a temperature of 20° C. to a suspension under inert gas of 1.845 g of lithium aluminum hydride and 5.25 g of aluminum chloride in 131 ml of tetrahydrofuran and the mixture was refluxed for 24 hours. After cooling to 0+5° C., 20 ml of ethyl acetate were added and then 100 ml of a saturated solution of sodium chloride were added. The suspension was filtered, then successively taken up in a water/6N HCl mixture (80 ml/50 ml), filtered, taken up in 60 ml of 60% ethanol and 8 ml of triethylamine and filtered. Water was added to the solution and precipitation was observed. Extraction was carried out with dichloromethane, followed by washing, drying, treating on L2S activated charcoal and concentration under reduced pressure until a dry extract of 1.9 g was obtained. This dry extract was dissolved at reflux in 60 ml of ethyl acetate and 4 drops of triethylamine for 15 minutes and then the solution was concentrated under reduced pressure to a volume of 30 ml, cooled over 1 hour to 0+5° C., separated and dried to obtain 1.03 g of the expected product melting at 177° C. and having a specific rotation of $[\alpha]_D = -80.6°$ (c=0.5% in EtOH).

Analysis: $C_{24}H_{38}ON_2$; molecular weight=370.56

|  | C | H | N |
|---|---|---|---|
| % calculated: | 77.78 | 10.34 | 7.56 |
| % found | 77.9 | 10.3 | 7.4 |

PHARMACOLOGICAL TESTS

METHOD

Preparation of the human spermatozoids

The human sperm originated from healthy donors. The mobile spermatozoids were separated by centrifugation on a Percoll gradient (47.5–95%) and then resuspended in a hypertonic BWW medium containing: 166 mM of NaCl, 5 mM of KCl, 1.3 mM of $CaCl_2$, 1.2 mM of $KH_2PO_4$, 1.2 mM of $MgSO_4$, 5.5mM of glucose, 21mM of sodium lactate, 0.25 mM of sodium pyruvate, 25 mM of $NaHCO_3$, 20 mM of Hepes and 0.8% of HSA (410 mosm/liter), pH 7.4 at ambient temperature.

Measurement of the intracellular calcium

The mobile spermatozoids were incubated for a minimum of 2 hours in the BWW/HSA capacitating medium and were then incubated at a concentration of $5-10\times10^6$/ml with Fura2-AM to a final concentration 2 μM at 37° C. for 45 minutes. After washing by centrifugation at 600 g for 10 minutes in BWW without HSA, the spermatozoids were suspended at a concentration of $4\times10^6$/ml. The florescence signal was measured at 37° C. using a spectrofluorimeter at excitation wave lengths of 340 and 380 nm (PTIM 2001-Kontron) or at 340, 360 and 380 nm (Hitachi F 2000 —B. Braun Science Tec.). The fluorescence emission was recorded at 505 nm. The progesterone or the products to be tested, dissolved in absolute ethanol, were added to the incubation medium at a final concentration of 0.1% of ethanol.

When an antagonistic effect of the progesterone was sought, the product was added to the medium 2 minutes before the progesterone. At the end of the each dosage, 5 μM of ionomycin were added to the sample to measure the maximum fluorescence signal. Then, the spermatozoids were permeabilized with 0.05% of Triton X-100 and 10 mM of EGTA were added (pH 9.5) to measure the minimum fluorescence signal. These values allowed the intracellular concentration of calcium ($[Ca^{2+}]i$) to be calculated by the method described by Grunkiewicz et al. 1985, J. Biol. Chem., Vol. 260, pp. 3440–3450). The results of the intracellular calcium concentra-tions were expressed relative to the basal level which was arbitrarily set equal to 1.

Sigma receptor: measurement of the relative bond affinity

The relative bond affinity was evaluated for preparations of rat brain and testicle membranes.

Preparation of the membranes

Male Sprague-Dawley rats originating from Iffa Credo and weighing approximately 200 g were used. The animals were scarified by decapitation and the brain and testicles were removed and homogenized in 10 to 25 volumes of 50 mM Tris-HCl buffer (pH 7.7) at 4° C. using an Ultrathurax. The homogenates were centrigued at 30,000 g for 15 minutes at 4° C. and the pellets were washed 3 times by resuspension in the same buffer and centrifugation under the same conditions. The membranes obtained in this way were stored at −80 C.

Incubation

The marker of the sigma receptors used was $^3$H PPP (propyl-3-(propyl-3-(3-hydroxyphenyl)-piperidine) of NEN having a specific activity of 3404 GBq/mmol. The membranes were suspended in the 50 mM Tris-HCl buffer, pH 8.0 to obtain a concentration of proteins of approximately 0.6 mg/ml for the testicles and 1 mg/ml for the brain. Aliquots of the homogenate were incubated for 90 minutes at 25° C. in a total volume of 0.5 ml with 3 nM of $^3$H PPP in the presence of increasing concentrations of reference product (haloperidol) or of the products to be tested. At the end of the incubation, the $^3$H PPP bound to the membranes was separated from the free $^3$H PPP by rapid filtration on Whatman GF/C filters pre-treated beforehand with 0.05% of polyethyleneimine. The precipitate was washed twice with 5 ml of Tris-HCl buffer and the radioactivity was counted after the addition of 20 ml of Aqualyte scintillating liquid (Baker).

Calculation of the relative bond affinity (RBA)

The following two curves were drawn: percentage of bound tritiated marker 100×B/BO as a function of the logarithm of the concentration of unlabelled reference product or as a function of the logarithm of the concentration of unlabelled test product. The straight line of the following equation was determined:

$I_{50}=100(BO/BO+Bmin/BO)/2$ i.e.

$I_{50}=100(1+Bmin/BO)/2=50(1+Bmin/BO)$

BO =concentration of the bound tritiated marker in the absence of any unlabelled product.

B=concentration of the bound tritiated marker in the presence of a concentration X of unlabelled product.

Bmin=concentration of the bound tritiated marker in the presence of a large excess of the unlabelled reference product (5,000 nM).

The intersections of the straight line $I_{50}$ and the curves allowed the evaluation of the concentrations of the unlabelled reference product (CH) and of the unlabelled test product (CX) which inhibited by 50% the specific binding of the tritiated marker on the receptor. The relative bond affinity (RBA) of the test product was determined by the equation:

RBA=100 (CH)/(CX).

The RBA of the haloperidol was arbitrarily set equal to 100.

PHARMACOLOGICAL TESTS

1—Relative bond affinity (RBA) for the Sigma receptor

|  | Brain (rat) | Testicle (rat) |
|---|---|---|
| Ref: Haloperidol | 100.0 | 100.0 |
| Progesterone | 0.7 | 0.3 |
| Estrone | <0.06 | <0.1 |
| Product of Example 1 (product U) | 4.3 | 58.0 |

2—Measurement of intracellular calcium

Effect of progesterone at $10^{-5}$ M after 2 minutes of pre-treatment with product U, at different doses $10^{-8}$ M to $10^{-5}$ M on [Ca$^{2+}$]i Mean+SEM n=3

| PROG. alone | U10$^{-8}$M + PROG. | U10$^{-7}$M + PROG. | U10$^{-6}$M + PROG. | U10$^{-5}$M + PROG. |
|---|---|---|---|---|
| 3.67 ± 0.97 | 3.33 ± 0.87 | 4.26 ± 1.93 | 2.63 ± 0.57 | 1.0 ± 0.0 |

The results were expressed relative to the basal level set equal to 1. Value of the basal level in the three experiments was 176.70±22.90 nM.

Antagonistic effect of the Product U at $10^{-5}$ M on the effect of PROG at $10^{-5}$ M. Mean±SEM n=8

| PROG. $10^{-5}$M alone | U10$^{-5}$M alone | Pre-treatment 2 mn with U10$^{-5}$M + PROG. $10^{-5}$M |
|---|---|---|
| 5.76 ± 0.84 | 0.95 ± 0.05 | 0.95 ± 0.05 |

The results were expressed relative to the basal level set equal to 1.

CONCLUSION

Effect on the intracellular calcium of human spermatozoids

Progesterone at the concentration of $10^{-5}$ M induced a transitory increase of the [Ca$^{2+}$]i followed by a second phase where the [Ca$^{2+}$]i was slightly greater than the basal level. As for Product U at $10^{-5}$ M, it completely antagonized the effect of progesterone when it was added to the medium 2 minutes before the progesterone.

Relative bond affinity (RBA) for the sigma receptor

Product U and progesterone were capable of displacing $^3$H PPP. The RBA's calculated using rat brain membranes had also been evaluated on testicles and are given in the table. The differences observed between the RBA's at the level of the brain and testicles could be explained by a different distribution of the various types of sigma receptor sites between these two organs. Such products could therefore inhibit the acrosomial reaction (essential stage of fertilization) in the case of antagonists such as Product U and could therefore be used as a male contraceptive.

Various modifications of the compounds and method of the invention may be made without departing from the spirit or scope thereof and it is to be understood that the invention is intended to be limited only as defined in the appended claims.

What is claimed is:

1. A method of controlling fertility in male warm-blooded animals comprising administering to male warm-blooded animals an amount of a compound selected from the group consisting of a 8α,9β,13α,14β compound of the formula

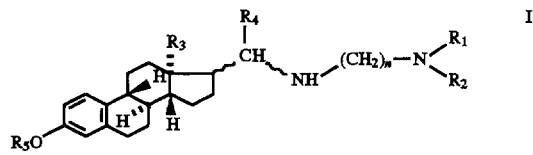

wherein $R_1$ and $R_2$ are individually selected from the group consisting of alkyl of 1 to 12 carbon atoms and aralkyl of 7 to 15 carbon atoms or taken together form a saturated heterocycle of 5 to 6 ring members optionally having a second ring heteroatom selected from the group consisting of sulfur, oxygen and nitrogen, $R_3$ is an α-alkyl of 1 to 8 carbon atoms, n is an integer from 2 to 15, $R_4$ is alkyl of 1 to 12 carbon atoms, $R_5$ is selected from the group consisting of hydrogen, alkyl of 1 to 12 carbon atoms and acyl of an organic carboxylic acid of up to 12 carbon atoms and the wavy lines indicate that the 17- and 20- asymmetrical centers are independent of the absolute R and S configurations and their non-toxic, pharmaceutically acceptable acid addition salts sufficient to control fertility of the animal.

2. The method of claim 1, wherein n is 2.

3. A method of claim 1, wherein the compound is selected from the group consisting of the formula

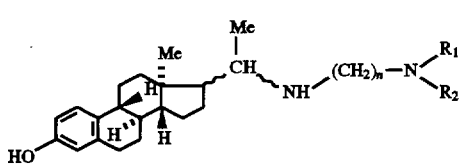

wherein $R_1$ and $R_2$ have the definitions of claim 1 and their non-toxic, pharmaceutically acceptable acid addition salts.

4. The method of claim 1 wherein the compound is selected from the group consisting of (20R) (8α,9β,13α,14β,17α) 20-[((dimethylamino)-ethyl)-amino]-19-nor-$\Delta^{1,3,5(10)}$-pregnatrien-3-ol, (20S) (8α,9β,13α,14β,17α) 20-[((dimethylamino)-ethyl)-amino]-19-nor-$\Delta^{1,3,5(10)}$-pregnatrien-3-ol, (20R) (8α,9β,13α,14β,17α) 20-[((dimethylamino)-ethyl)-amino]-19-nor-$\Delta^{1,3,5(10)}$-pregnatrien-3-ol, (20S) (8α,9β,13α,14β,17α) 20-[((dimethylamino)-ethyl)-amino]-19-nor-$\Delta^{1,3,5(10)}$-pregnatrien-3-ol and their non-toxic, pharmaceutically acceptable acid addition salts.

5. The method of claim 1 wherein the compound is (20S) (8α,9β,13α,14β,17α) 20-[((dimethylamino)-ethyl)-amino]-19-nor-$\Delta^{1,3,5(10)}$-pregnatrien-3-ol or its non-toxic, pharmaceutically acceptable acid addition salt.

* * * * *